US012311077B2

(12) United States Patent
Chen et al.

(10) Patent No.: US 12,311,077 B2
(45) Date of Patent: May 27, 2025

(54) METHOD OF MAKING, MANUFACTURING OR PRODUCING ORTHOPEDIC SOFT TISSUE

(71) Applicant: NEW YORK SOCIETY FOR THE RELIEF OF THE RUPTURED AND CRIPPLED, MAINTAINING THE HOSPITAL FOR SPECIAL SURGERY, New York, NY (US)

(72) Inventors: Tony Chen, Highland Park, NJ (US); Suzanne A. Maher, Highland Lakes, NJ (US); Russell Warren, Greenwich, CT (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 1315 days.

(21) Appl. No.: 16/757,191

(22) PCT Filed: Oct. 19, 2018

(86) PCT No.: PCT/US2018/056642
§ 371 (c)(1),
(2) Date: Apr. 17, 2020

(87) PCT Pub. No.: WO2019/079678
PCT Pub. Date: Apr. 25, 2019

(65) Prior Publication Data
US 2021/0038766 A1 Feb. 11, 2021

Related U.S. Application Data

(60) Provisional application No. 62/574,524, filed on Oct. 19, 2017.

(51) Int. Cl.
*A61F 2/38* (2006.01)
*A61L 27/16* (2006.01)
(Continued)

(52) U.S. Cl.
CPC ........ *A61L 27/3662* (2013.01); *A61F 2/3872* (2013.01); *A61L 27/16* (2013.01);
(Continued)

(58) Field of Classification Search
CPC .. A61L 27/3662; A61L 27/16; A61L 2430/06; A61L 2430/10; A61F 2/3872;
(Continued)

(56) References Cited

U.S. PATENT DOCUMENTS

| 4,880,429 A | 11/1989 | Stone |
| 5,376,110 A | 12/1994 | Tu et al. |

(Continued)

FOREIGN PATENT DOCUMENTS

| JP | H 7-505792 | 6/1995 |
| JP | H 10-501155 | 2/1998 |

(Continued)

OTHER PUBLICATIONS

Japanese OA in JP Application No. 2020-518752, mailed Dec. 2, 2022 (14 pages) an English Translation attached hereto.
(Continued)

*Primary Examiner* — Nahida Sultana
*Assistant Examiner* — Mohamed K Ahmed Ali
(74) *Attorney, Agent, or Firm* — Leason Ellis LLP

(57) ABSTRACT

An improved method of making, manufacturing and/or producing engineered orthopedic soft tissue including cartilage, meniscus, annulus fibrosus, and tendon/ligaments which results in engineered soft tissue in which the fibers are aligned the same or nearly the same as naturally occurring
(Continued)

tissue. The present invention also includes molds and other apparatus for carrying out the methods of the invention and kits.

17 Claims, 10 Drawing Sheets

(51) Int. Cl.
| | |
|---|---|
| *A61L 27/22* | (2006.01) |
| *A61L 27/24* | (2006.01) |
| *A61L 27/36* | (2006.01) |
| *A61L 27/50* | (2006.01) |
| *B29C 33/30* | (2006.01) |
| *B29C 35/08* | (2006.01) |
| *B29C 35/16* | (2006.01) |
| *B29C 39/04* | (2006.01) |
| *B29C 39/38* | (2006.01) |
| *C08L 5/08* | (2006.01) |
| *C08L 29/04* | (2006.01) |
| *B29K 29/00* | (2006.01) |

(52) U.S. Cl.
CPC ............ *A61L 27/227* (2013.01); *A61L 27/24* (2013.01); *A61L 27/3654* (2013.01); *A61L 27/3687* (2013.01); *A61L 27/3691* (2013.01); *A61L 27/50* (2013.01); *B29C 33/301* (2013.01); *B29C 35/08* (2013.01); *B29C 35/16* (2013.01); *B29C 39/04* (2013.01); *B29C 39/38* (2013.01); *C08L 5/08* (2013.01); *C08L 29/04* (2013.01); *A61L 2430/06* (2013.01); *A61L 2430/10* (2013.01); *B29C 2035/0827* (2013.01); *B29K 2029/04* (2013.01); *B29K 2995/0056* (2013.01)

(58) Field of Classification Search
CPC ....... B29C 33/301; B29C 35/08; B29C 35/16; B29C 39/04; B29C 39/38
See application file for complete search history.

(56) References Cited

U.S. PATENT DOCUMENTS

| | | | |
|---|---|---|---|
| 2005/0221703 | A1 | 10/2005 | Stone |
| 2010/0023130 | A1 | 1/2010 | Henry et al. |
| 2011/0093073 | A1* | 4/2011 | Gatt ................... A61F 2/30756 623/23.72 |
| 2016/0213812 | A1 | 7/2016 | Pathak et al. |
| 2016/0228604 | A1 | 8/2016 | Mann et al. |
| 2017/0224459 | A1 | 8/2017 | Stuckensen et al. |
| 2017/0224498 | A1 | 8/2017 | Mccullen et al. |

FOREIGN PATENT DOCUMENTS

| | | |
|---|---|---|
| JP | 2005529682 | 12/2003 |
| JP | 2004-535242 | 11/2004 |
| JP | 2009508540 | 3/2009 |
| WO | 03105737 | 12/2003 |
| WO | WO 2006/102756 | 10/2006 |
| WO | 2007020449 A2 | 2/2007 |

OTHER PUBLICATIONS

Notice of Reasons for Refusal in corresponding Japanese Patent Application No. 2020-518752 dated Sep. 27, 2023. 7 pages. English translation attached.

* cited by examiner

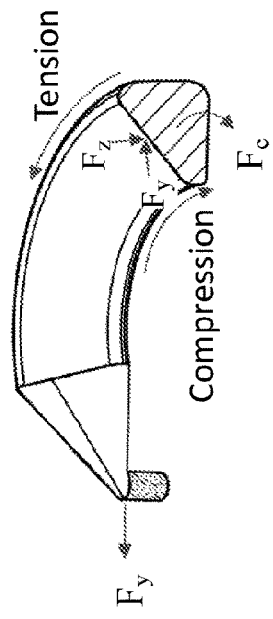
Figure 1B
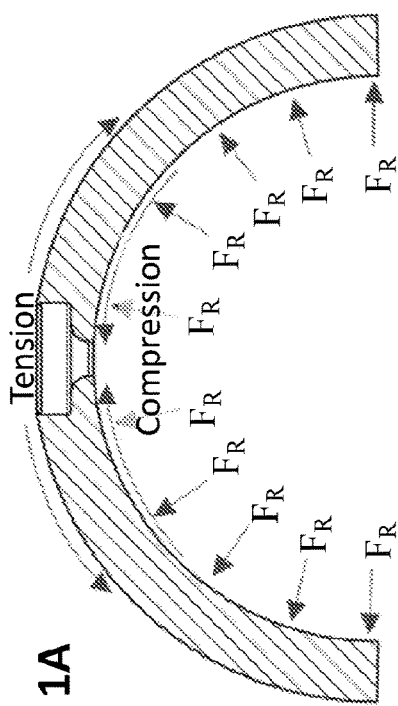
Figure 1A
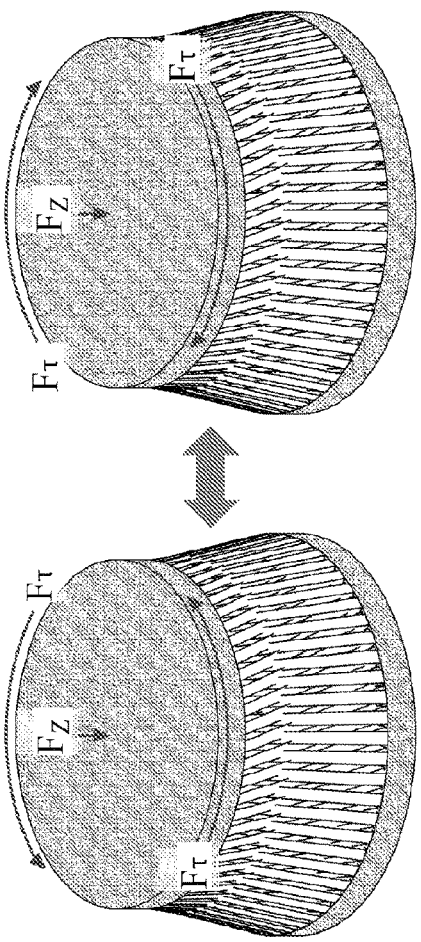
Figure 1D
Figure 1C

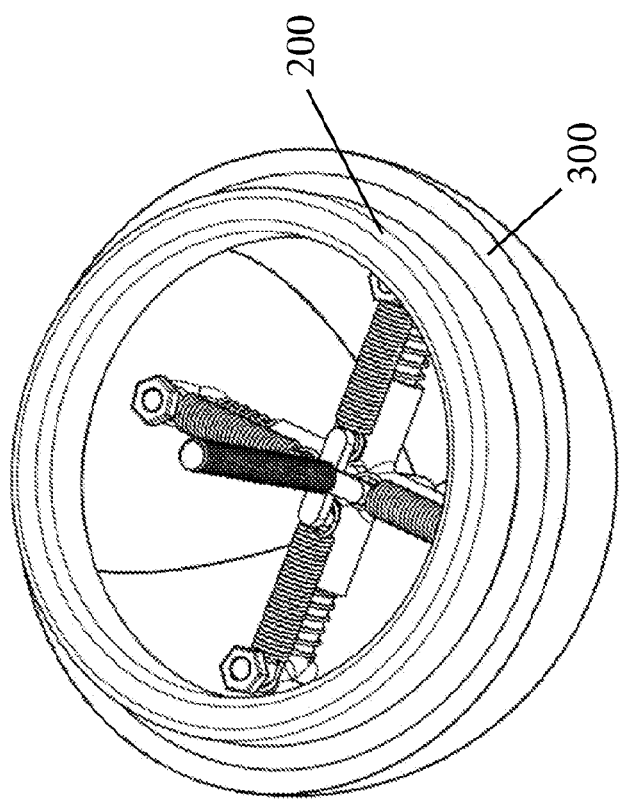
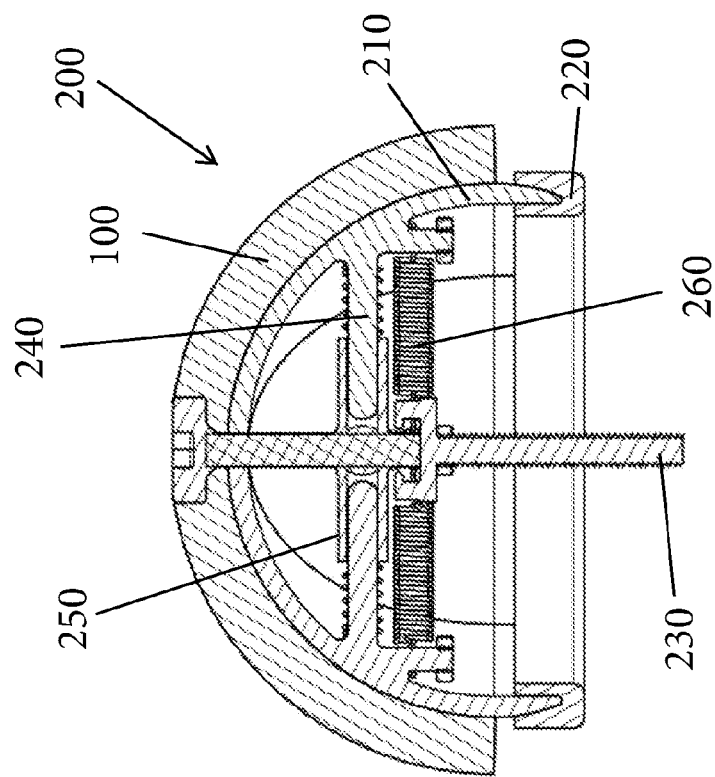
Figure 2A
Figure 2B

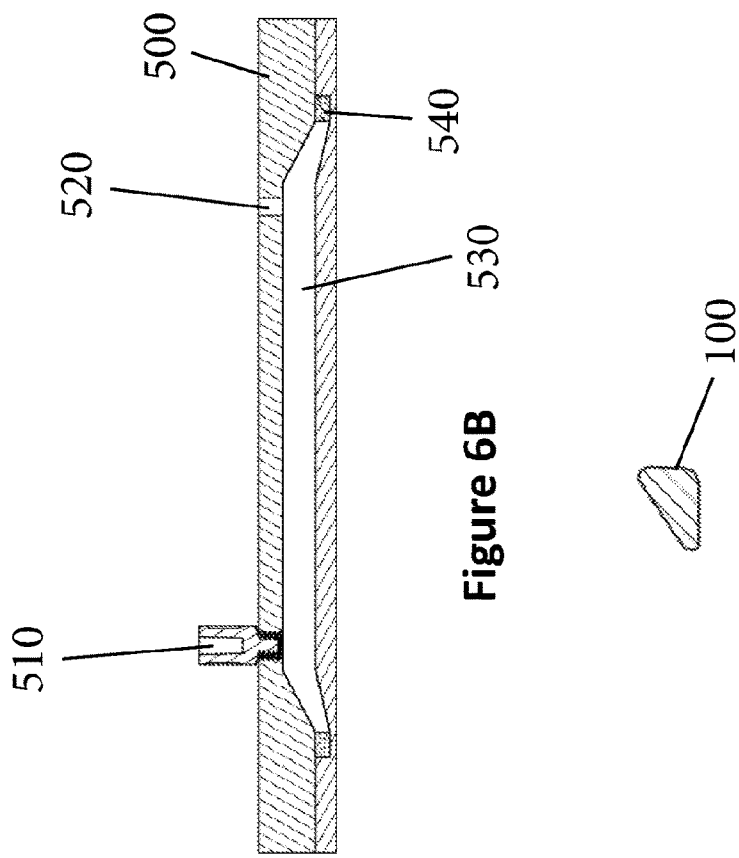
Figure 6B
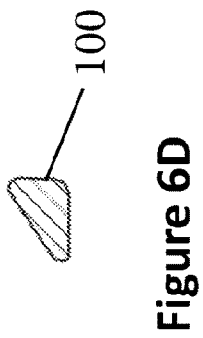
Figure 6D
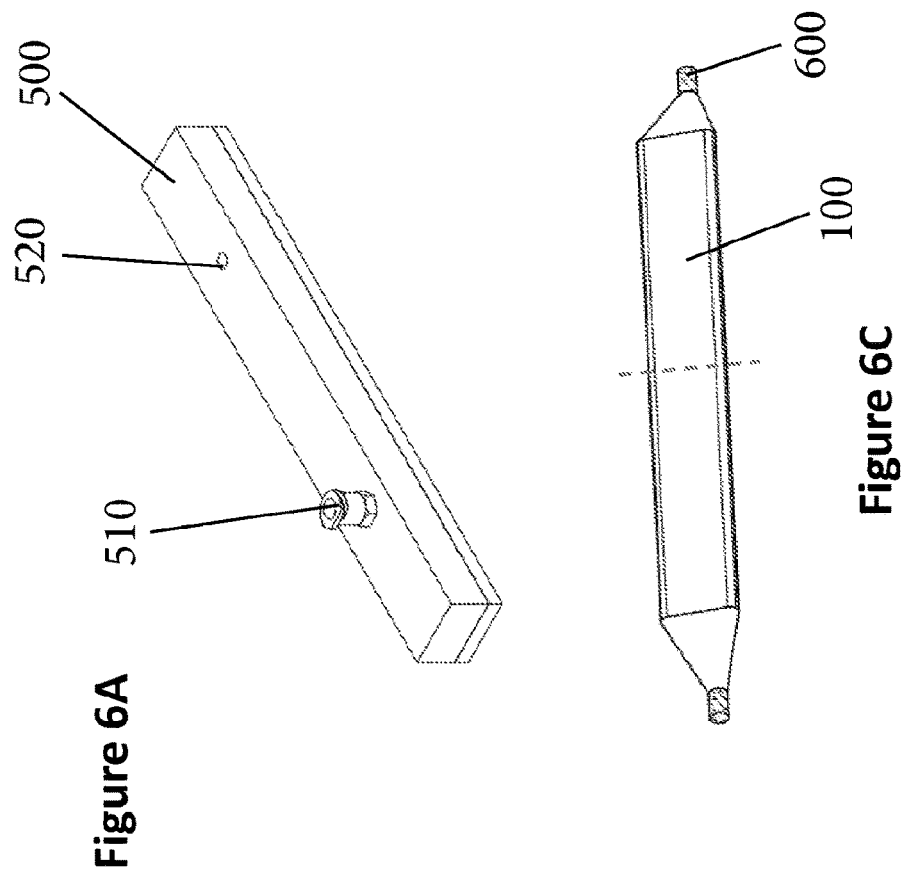
Figure 6A
Figure 6C

METHOD OF MAKING, MANUFACTURING OR PRODUCING ORTHOPEDIC SOFT TISSUE

RELATED APPLICATION

The present application is a U.S. National Phase Application under 35 U.S.C. § 371 of International Patent Application No. PCT/US2018/056642, filed Oct. 19, 2018, which claims priority to U.S. Patent Application Ser. No. 62/574,524, filed Oct. 19, 2017, each of which is incorporated by reference as if expressly set forth in their respective entirety herein.

FIELD OF THE INVENTION

The present invention relates to an improved method of making, manufacturing and/or producing engineered orthopedic soft tissue including cartilage, meniscus, annulus fibrosus, and tendon/ligaments using synthetic and natural polymers. The method results in engineered soft tissue in which the fibers are aligned the same or nearly the same as naturally occurring tissue.

The present invention also includes molds and other apparatus for carrying out the methods of the invention.

BACKGROUND OF THE INVENTION

Joint loading plays an important role in the development and properties of tissue in the body. One place where this is most evident is the extracellular matrix of cartilage where there are distinct zones of collagen fiber alignment through the depth of the tissue. Cartilage comprises three zones: a superficial tangential zone furthest from the bone which is about 10-20% of the tissue; a middle zone which is about 40-60% of the tissue; and a deep zone which is about 30% of the tissues. While physiological forces have been applied to try to recreate this alignment, to date, there has been no success in fully recapitulating this structure. Observations of cartilage postnatally have shown the development of this defined architecture in situ before the application of loading, opening the possibility that other constraints are driving the architecture. One such factor is the rapid cellular growth and maturation postnatally.

The current invention uses these observations to create an engineered cartilage and other orthopedic soft tissue that mimics native tissue.

SUMMARY OF THE INVENTION

The present invention overcomes the problems in the art by providing a novel method for making, manufacturing and/or producing engineered orthopedic soft tissue comprising applying force(s) to a partially crosslinked polymer and applying additional crosslinking to the polymer while the force(s) is applied, under conditions and for a time to allow the fiber orientation of the engineered orthopedic soft tissue to mimic or recapitulate the fiber orientation of naturally occurring orthopedic soft tissue.

In some embodiments, the orthopedic soft tissue is cartilage and the cartilage is articular.

In further embodiments, the orthopedic soft tissue is meniscus, annulus fibrosus, or tendon/ligament.

In some embodiments, the orthopedic soft tissue is independent. In some embodiments, the orthopedic soft tissue is attached to another cryogel, polymer, or hydrogel, to at least one rigid porous base made of materials such as porous PEEK or porous titanium, and/or to native tissue.

In some embodiments, the invention provides for a method to make, manufacture and/or produce engineered cartilage, comprising the steps of:
  a. placing a uniform layer of a polymer on the surface of a mold, wherein the mold is shaped as a hemisphere;
  b. partially crosslinking the polymer;
  c. placing the partially crosslinked polymer and the mold onto an expander, wherein the expander is shaped as a hemisphere and is capable of radially expanding the polymer on the mold;
  d. crosslinking the polymer while the expander is radially expanding the polymer; and
  e. removing the polymer from the mold.

In some embodiments, the invention provides for a method to make, manufacture and/or produce engineered meniscus, comprising the steps of:
  a. casting a polymer in a negative mold, wherein the mold contains an inlet port in which to inject the polymer, an area to contain the polymer, and an area for at least one rigid porous base;
  b. partially crosslinking the polymer;
  c. removing the polymer and the at least one rigid porous base from the mold;
  d. placing the partially crosslinked polymer and the at least one rigid porous base onto a loading frame, wherein the loading frame contains a post and at least one screw for keeping the polymer and rigid porous base in place, and a crank for applying force to the polymer;
  e. crosslinking the polymer; and
  f. removing the polymer and the rigid porous base from the loading frame.

In some embodiments, the polymer is crosslinkable and includes but is not limited to poly(vinyl alcohol), polyurethane, polycarbonate urethane, ultrahigh molecular weight polyethylene, polyacrylic acid, collagen, chitosan, hyaluronic acid or any other synthetic or natural polymer.

In some embodiments, the crosslinking is done by one or more freeze/thaw cycles, the application of a chemical crosslinking agent, and/or UV light exposure.

The present invention also provides for the engineered orthopedic soft tissue made, manufactured and/or produced by the methods described herein.

The present invention also provides for molds and expanders and other apparatus for carrying out the methods.

The present invention also provides for kits.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 1 shows schematics of applying forces to polymers when making, manufacturing or producing engineered articular orthopedic soft tissue. FIG. 1A shows the forces being applied to recreate cartilage. FIG. 1B shows the forces being applied to recreate meniscus. FIG. 1C shows the forces applied to recreate the annulus fibrosus. FIG. 1D shows the forces required to recreate tendon and ligament.

FIG. 2 illustrates an exemplary mold for use in making, manufacturing or producing engineered cartilage. FIG. 2A is a cross-sectional side view of the mold. FIG. 2B illustrates an exemplary container with the exemplary mold inside.

FIG. 4 illustrates an exemplary mold for use in making, manufacturing or producing engineered cartilage using radial forces in the four units that make up the mold.

FIG. 5 shows that the engineered cartilage of the invention is similar in fiber alignment to naturally occurring cartilage.

FIG. 6 illustrates an exemplary mold for use in making, manufacturing or producing engineered meniscus. FIG. 6A is a top view of the mold. FIG. 6B is a side cross-sectional view of the mold. FIG. 6C is the polymer and rigid porous base after removal from the mold. FIG. 6D is a cross-section of the polymer after removal from the mold.

FIG. 7 illustrates an exemplary loading frame for use in making, manufacturing or producing engineered meniscus.

DETAILED DESCRIPTION OF INVENTION

Definitions

Figure 3:
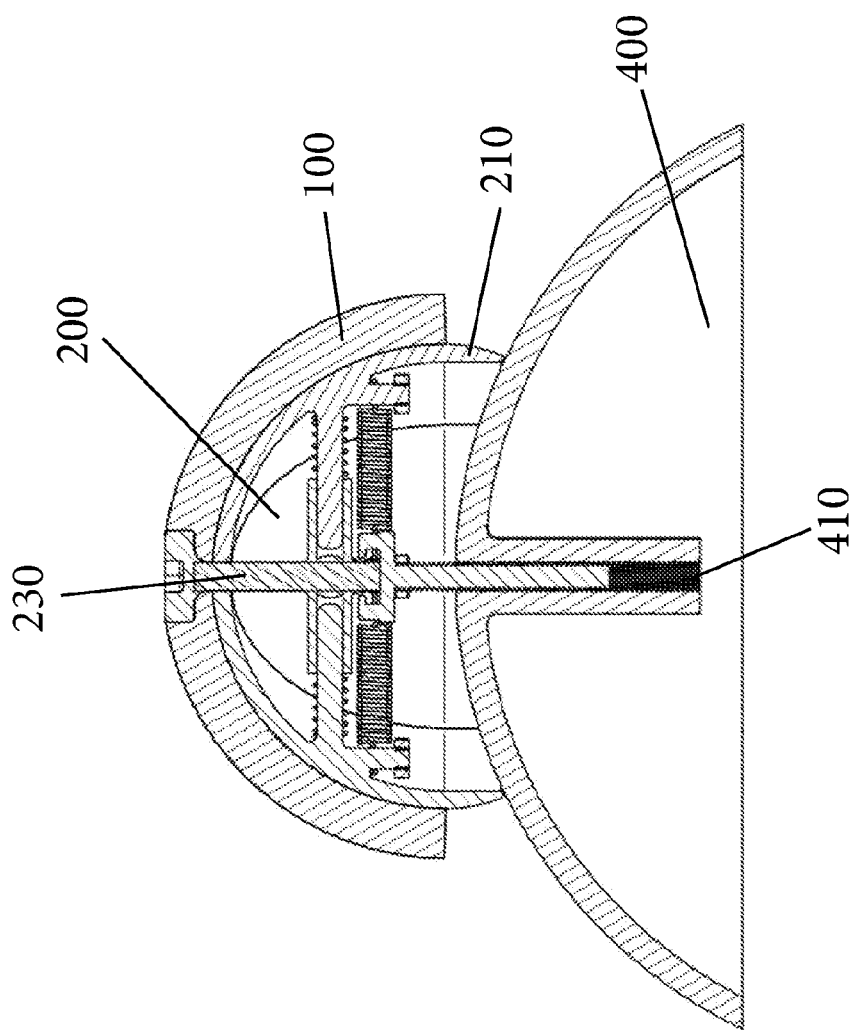
FIG. 3 illustrates an exemplary expander for use in making, manufacturing or producing engineered cartilage.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The terms "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "polymer" means a large molecule composed of repeating structural units often connected by covalent chemical bonds. Polymers can be natural or synthetic.

The term "cryogel" means a polymer material that is crosslinked for example by repeated freeze/thaw cycles ranging from 1 to 10 cycles.

As discussed above, there has been no success to date in engineering cartilage and other orthopedic soft tissue that recapitulates or mimics the fiber alignment of naturally occurring tissue. It was hypothesized that the rapid growth and maturation of the cells in the cartilage is a factor in the development of cartilage architecture and that as cells divide and mature the forces on the cartilage will dictate the growth and alignment of the collagen, i.e., fibers, in cartilage.

Using this concept, methods and systems were created which apply force, e.g., compression, tension, etc., to polymers during which the polymers are being crosslinked. These methods and systems result in engineered cartilage and other orthopedic soft tissue which recapitulates or mimics naturally occurring orthopedic soft tissues including cartilage (see FIG. 5) and engineered meniscus that recapitulates or mimics naturally occurring meniscus (see FIG. 8).

Methods for Making, Manufacturing and/or Producing Engineered Soft Orthopedic Tissue The current method of the invention of applying forces in multiple directions on partial crosslinked cryogels, chemically crosslinked polymers, and UV crosslinked polymers can be used to mimic the fiber alignment of various orthopedic soft tissues and can be used to make, manufacture and/or produce various engineered orthopedic soft tissues including but not limited to including cartilage (FIG. 1A), meniscus (FIG. 1B), annulus fibrosus (FIG. 1C), and tendon/ligament (FIG. 1D). The methods of the invention can be performed to cryogels and crosslinkable polymers independently as well as those attached to another cryogel/polymer and/or to at least one rigid porous base, such as porous PEEK or porous titanium.

As shown in FIG. 1, various forces are necessarily applied to the polymer while crosslinking the polymers, either partially or completely, depending upon the type of orthopedic soft tissue being made.

FIG. 1A shows the forces that can be applied when crosslinking the polymers and making, manufacturing and/or producing engineered cartilage including articular. These forces include radial force ($F_R$) applied under the polymer as well as those that create tension on the surface of the polymer and compression at the base of the polymer. The method exemplified in Example 2 use these forces while crosslinking the polymer resulting in an engineered cartilage with fiber alignment similar to native cartilage (FIG. 5).

Figure 8:
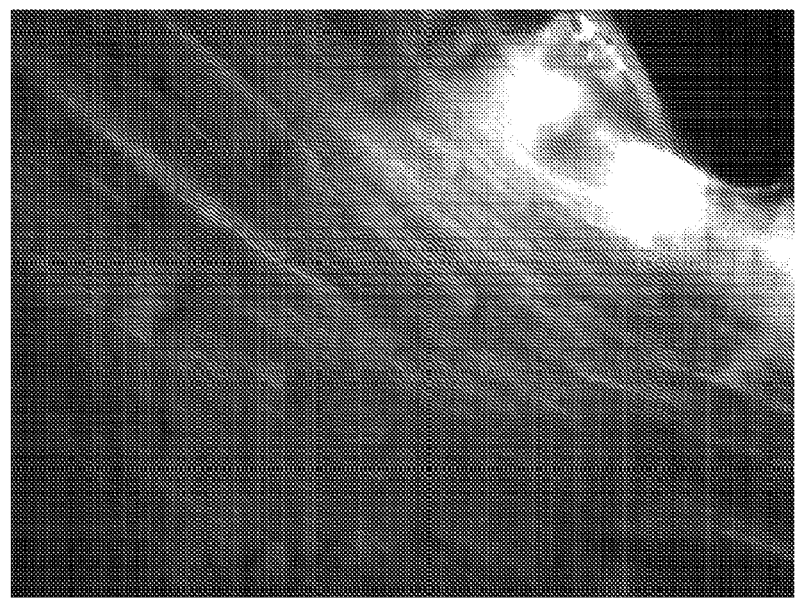
FIG. 8 is a polarized image of a 100 μm thick slice of an engineered meniscus.

FIG. 1B shows the forces that can be applied when crosslinking the polymers and making, manufacturing and/or producing engineered meniscus. These forces include circumferential ($F_C$), forces in the Y ($F_Y$) and Z ($F_Z$) direction, as well as tension and compression. Additionally when making engineered meniscus, the polymer can be attached to at least one rigid porous base. The method exemplified in Example 4 use these forces while crosslinking the polymer resulting in an engineered meniscus with fiber alignment similar to native meniscus (FIG. 8).

FIG. 1C shows the forces applied when crosslinking the polymers and making, manufacturing and/or producing engineered annulus fibrosus including torsional (Fτ) and forces in the Z direction ($F_Z$).

FIG. 1D shows the forces applied when crosslinking the polymers and making, manufacturing and/or producing engineering tendons and ligaments including torsional (Fτ) and forces in the Z direction ($F_Z$). Additionally when making engineered tendons and ligaments, the polymer can be attached to at least one porous base.

In all of the above methods, the polymer used should be crosslinkable and include but is not limited to poly(vinyl alcohol) (PVA), polyurethane, polycarbonate urethane, ultrahigh molecular weight polyethylene, polyacrylic acid, collagen, chitosan, hyaluronic acid or any other synthetic or natural polymer. PVA is a preferred polymer.

In all of these methods, the crosslinking is done by one or more freeze/thaw cycles, chemical crosslinking, and/or UV light exposure.

In all of these methods, the preferred method for freezing/thawing includes ramping the temperature to about −20° C. at a rate of about 0.5° C./minute and freezing the polymer at about −20° C. for about 4 to about 24 hours, with 20 hours being preferred and then ramping the temperature to about 20° C. at a rate of about 0.5° C./minute and thawing the polymer at about 20° C. for about 4 to about 12 hours, with 4 hours being preferred. Again this can be varied by a person of skill in the art. Both the number of hours of freezing and/or thawing can be varied as well as the number of cycles and the amount of strain (see Table 1).

In all of these methods, the preferred method for UV crosslinking is to partially crosslink the polymer using a 405 nm laser with liquid polymer at 30° C. to crosslink 60% of the reactive groups. This method can be performed using a negative mold or by stereolithography 3D printing. The amount of strain and the number of strain cycles can be varied to achieve the final structure.

In all of these methods, the preferred method for chemical crosslinking is to partially crosslink the polymer with either 10% formaldehyde, paraformaldehyde, or glutaraldehyde for about 0.5 hours to about 2 hours. Again this can be varied by a person of skill in the art. Both the concentration of chemical crosslinking agent and duration of exposure can be varied.

Additionally, the following parameters can also be varied to dictate the amount of polymer fiber alignment and it is within the skill of the art to determine how to vary the parameters to obtain the desired engineered soft orthopedic tissue with the desired fiber alignment.

TABLE 1

Parameters for Polymer Fiber Alignment in Making Engineered Soft Orthopedic Tissue

| Parameter | Minimum | Maximum | Ideal Values for Cartilage | Ideal Values for Meniscus | Effect |
| --- | --- | --- | --- | --- | --- |
| Temperature Ramp Rate | 0.2° C./min | 120° C./min | 0.5° C./min | 0.5° C./min | Allows for longer polymer relaxation time decreasing the residual strain in the fibers. Longer temperature ramp rates decrease the non-uniform freeze and thaw of the polymers |
| Strain Rate | 1%/sec | 1%/30 min | 1%/sec | 5%/sec | Increasing the strain rate increases alignment and residual strains |
| % Strain | 30% | 200% | 40% | 30% | Increasing strain increases fiber alignment |
| Multiple Strain Cycles (one per crosslinking cycle) | 1 | 5 | 1 | 2 | Increasing the number of strain cycles increases the amount of aligned polymer |
| Polymer Concentration | 10% | 40% | 20% | 20% | Increasing polymer concentration increases modulus and also number of aligned fibers |

Strain Cycle = how many times the polymer is stretched. For example, generally the polymer is stretched only once after the first freeze/thaw cycle but the polymer could be stretched again after the second freeze/thaw cycle to create more aligned fibers.
% Strain = the % deformation of the polymer from its original shape
Strain rate = the % strain to apply over time until the desired % strain is reached Methods and Systems for Making, Manufacturing and/or Producing Engineered Cartilage FIG. 1A shows the forces that can be applied when crosslinking the polymers and making, manufacturing and/or producing engineered cartilage, including articular.

A method for making, manufacturing or producing cartilage using radial forces as well as generating tensile and compressive forces (see FIG. 1A) can comprise the following steps: (reference to FIGS. 2 and 3):

a. placing a mold 200 into a hemispherical container 300 wherein the mold 200 is shaped like a hemisphere and comprises at least one leaflet 210 and preferably a plurality such as 4, and a leaflet collar 220 that receives and surrounds a free end of the leaflet;

b. pouring a liquid polymer into the container 300 wherein the container 300 surrounds the mold 200;

c. partially crosslinking the polymer to form a polymer structure 100;

d. removing the mold 200 and polymer 100 from the container 300 and removing the leaflet collar 220;

e. placing the mold 200 and the polymer 100 onto an expander 400 wherein the expander contains a central threaded channel 410 (defined in a central boss/protrusion of the expander 400) in which the central post 230 of the mold 200 is threaded f. advancing the expander 400 towards the mold 200 with the polymer 100 of the mold 200 on the surface by screwing the expander 400 up the central post 230 until the desired expansion is reached (radial expansion of the mold is possible due to the construction of the mold);

g. crosslinking the polymer 100 after the expander 400 has radially expanded the mold 200 and polymer 100; and h. removing the polymer from the mold.

In some embodiments, the partial crosslinking in step b. is done by freeze/thaw cycle, about 1 to about 3 cycles, preferably 1 cycle, or by UV light exposure for about 10 seconds to about 30 seconds or by exposure to a chemical crosslinking agent.

In some embodiments, the crosslinking in step d. is done by freeze/thaw cycles, about 3 to about 5 cycles, preferably 5 cycles or by UV light exposure preferably about 15 minutes to about 60 minutes or by exposure to a chemical crosslinking agent.

In some embodiments, the leaflet expander is advanced up the central post preferably about 1 mm to about 5 mm. The radius of the expander can be varied to change the strain rate and final percent strain, with a preferable radius of the expander being about 25 mm to about 100 mm.

A system for making, manufacturing or producing cartilage can comprise a mold 200, a container 300, an expander 400, and a polymer 100. Additionally, the system can comprise subsystems crosslinking the polymer either by freeze/thaw or UV light or chemical crosslinking agent.

In all of the above methods and systems, the polymer used should be crosslinkable and include but is not limited to poly(vinyl alcohol) (PVA), polyurethane, polycarbonate urethane, ultrahigh molecular weight polyethylene, polyacrylic acid, collagen, chitosan, hyaluronic acid or any other synthetic or natural polymer. PVA is a preferred polymer. The concentration of the polymer is ranges from about 10% to about 40%, with 20% being ideal. The polymer is preferably in a liquid state.

In all of these methods, the preferred method for freezing/thawing includes ramping the temperature to about −20° C. at a rate of about 0.5° C./minute and freezing the polymer at about −20° C. for about 4 to about 24 hours, with 20 hours being preferred and then ramping the temperature to about 20° C. at a rate of about 0.5° C./minute and thawing the polymer at about 20° C. for about 4 to about 12 hours, with 4 hours being preferred. Again this can be varied by a person of skill in the art. Both the number of hours of freezing and/or thawing can be varied as well as the number of cycles (see Table 1).

The ideal parameters for this method are found in Table 1 in the column for cartilage.

It will be appreciated that other types of devices other than the expander 400 can be used to apply the targeted forces to the polymer in the manner described herein.

Mold and Expander for a Method for Making, Manufacturing and/or Producing Engineered Cartilage A further aspect of the current invention is the unique mold and expander used in the method of making, manufacturing and/or producing engineered articular cartilage using radial forces.

In one embodiment shown in FIG. 2A, the mold is composed of: at least one leaflet 210 containing a leaflet compression spring rod 240 and a tension spring 260; a leaflet collar 220, a central post 230 containing at least one compression spring tube 250 (which has a number of outwardly extending arms about which spring rods 240 are disposed).

Figure 4B:
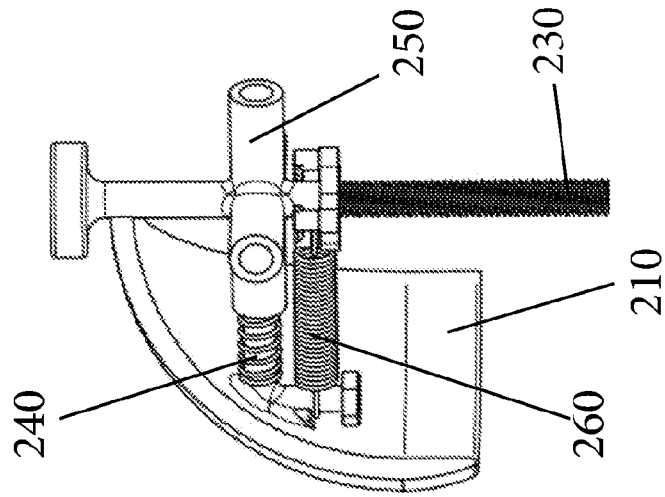
FIG. 4B is a cross-sectional view of the mold assembled.
Figure 4A:
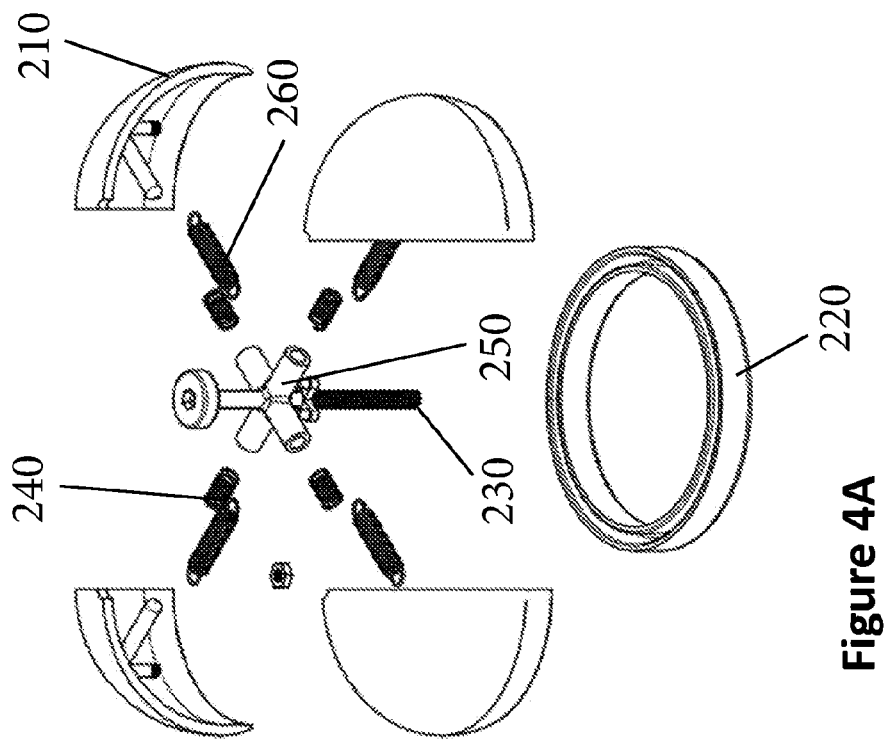
FIG. 4A is an exploded view of the mold components.

In one embodiment shown in FIG. 4, the illustrated mold 200 is composed of four leaflet units, each comprising a leaflet 210, a leaflet compression spring rod 240, and a tension spring 260 (the spring tube 250 is also configured to attach to one end of the spring 260, while the other end of spring 260 is coupled to the leaflet 210 so as to apply a biasing force to the leaflet) that are assembled radially and held together by a leaflet collar 220 to form a mold that is a hemisphere. The collar 220 has an annular shaped groove which receives bottom portions of the leaflets. See also FIG. 2B.

The mold is used in conjunction with a hemispherical leaflet expander 400.

In one embodiment of the expander shown in FIG. 3, the expander 400 contains a threaded channel 410 in which the central post 230 of the mold is threadingly received for coupling the mold 200 to the expander 400.

The mold 200 and expander 400 can be made using traditional manufacturing from Teflon, PEEK, PEKK, polycarbonate or ULTEM with polycarbonate being the preferred material. The mold and expander can also be manufactured using newer technologies such as 3D printing.

Additionally, the mold 200 and expander 400 can be made of material able to withstand freezing temperatures, change in temperatures, chemical crosslinking agents, and exposure to UV light.

Each leaflet 210 is made with a preferable radius of about 10 mm to about 50 mm. The expander 400 is made with a preferable radius of about 25 mm to about 100 mm. The inner radius of the hemispherical container can be varied to create different thicknesses of polymer on the surface of the mold, preferably about 11 mm to about 60 mm.

Methods and Systems for Making, Manufacturing and/or Producing Engineered Meniscus FIG. 1B shows the forces that can be applied when crosslinking the polymers and making, manufacturing and/or producing engineered meniscus.

Figure 7B:
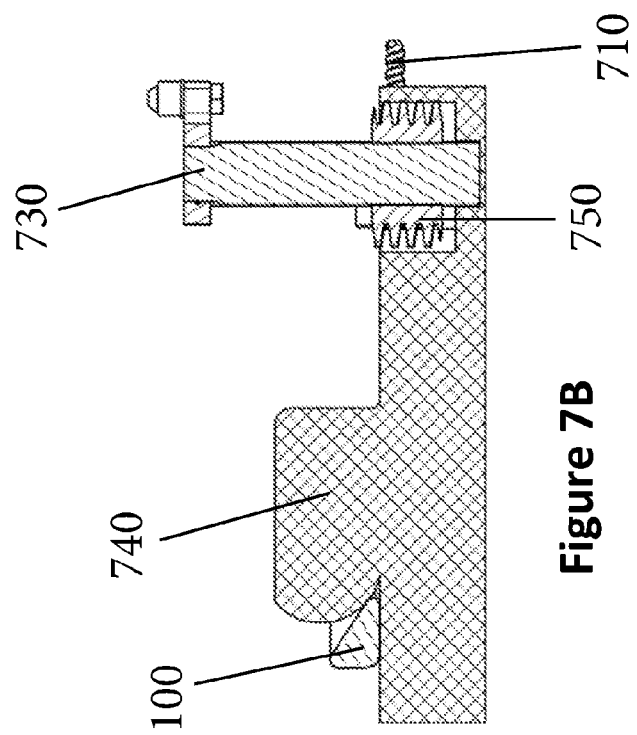
FIG. 7B is a side view of the loading frame.
Figure 7A:
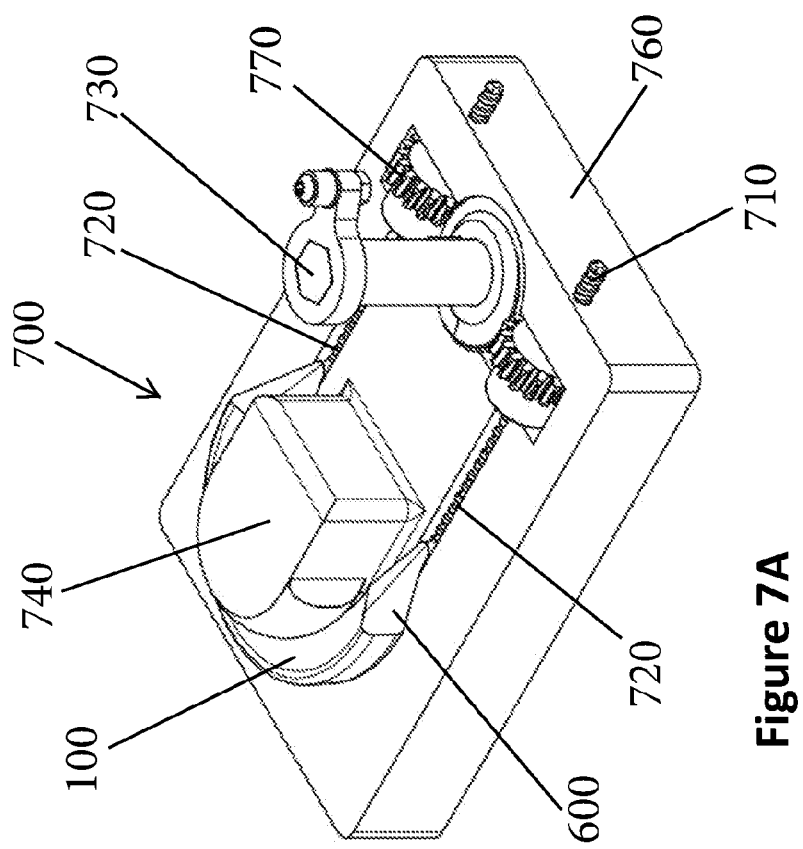
FIG. 7A is a top view of the loading frame.
Figure 7D:
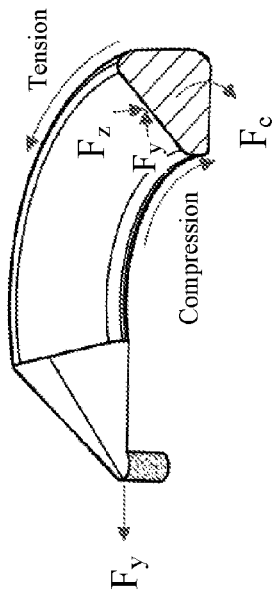
FIG. 7D shows the forces applied to the polymer when the loading frame is used.

A method for making, manufacturing or producing meniscus using forces in the X, Y, and Z direction as well as tensile and compressive (see FIG. 1B) can comprise the following steps: (reference to FIGS. 6 and 7):

a. injecting a liquid polymer into an inlet port 510 of a mold 500 until the liquid polymer starts to flow from the outlet port 520 of the mold 500, the mold 500 being in the desired shape of the polymer and having the inlet port 510, the outlet port 520, an area (cavity) 530 for the polymer 100 and an area (cavity) 540 for rigid porous bases 600;

b. partially crosslinking the polymer 100;

c. removing the partially crosslinked polymer 100 attached to the rigid porous bases 600 on each end (see FIG. 6C) from the mold 500;

d. placing the partially crosslinked polymer 100 and the rigid porous bases 600 into a loading frame 700;

e. fixing the rigid porous bases 600 to lead screws 710 on either side of the loading frame 700 using set screws 720 (e.g., FIG. 7D shows one base 600 including a downwardly extending protrusion (pin) that can be received in a corresponding hole);

f. turning the crank 730 of the loading frame 700 clockwise (a first direction) to cause the rigid porous bases 600 to move toward the crank 730 (as indicated by the arrows in FIG. 7C) which in turn causes a tensile force at the ends of the partially crosslinked polymer 100 and forces the polymer 100 against the post 740 that creates radial ($F_y$), axial ($F_z$), circumferential ($F_c$), compressive and tensile forces (see FIGS. 7C and 7D) (as shown, the pulling of the polymer into contact with post 740 results in the polymer wrapping around one end of the post 740 and extending along the sides thereof);

g. crosslinking the polymer 100; and h. removing the polymer 100 from the loading frame 700.

In some embodiments, the partial crosslinking in step b. is done by freeze/thaw cycle, about 1 to about 3 cycles, preferably 1 or by UV light exposure 10-30 seconds or by exposure to a chemical crosslinking agent.

In some embodiments, the crosslinking in step d. is done by freeze/thaw cycles, about 3 to about 5 cycles, preferably 5 or by UV light exposure preferably about 15 minutes to about 60 minutes or by exposure to a chemical crosslinking agent.

The crosslinking step g. is performed after the polymer has been stretched to about 20% to about 50% strain, preferably 30%.

A system for making, manufacturing or producing meniscus can comprise a mold 500, a loading frame 700, at least one rigid porous base 600, and a polymer 100. Additionally, the system can comprise subsystems for injecting the polymer, and crosslinking the polymer either by freeze/thaw or UV light or by exposure to a chemical crosslinking agent.

In all of the above methods and systems, the polymer used should be crosslinkable and include but is not limited to poly(vinyl alcohol) (PVA), polyurethane, polycarbonate urethane, ultrahigh molecular weight polyethylene, polyacrylic acid, collagen, chitosan, hyaluronic acid or any other synthetic or natural polymer. PVA is a preferred polymer. The concentration of the polymer is ranges from about 10% to about 40% with 20% being ideal. Ideally the polymer should be in liquid form.

The polymer can be injected into the inlet port 510 of the mold 500 with a syringe.

In all of these methods, the preferred method for freezing/thawing includes ramping the temperature to about −20° C. at a rate of about 0.5° C./minute and freezing the polymer at about −20° C. for about 4 to about 24 hours, with 20 hours being preferred and then ramping the temperature to about 20° C. at a rate of about 0.5° C./minute and thawing the polymer at about 20° C. for about 4 to about 12 hours, with 4 hours being preferred. Again this can be varied by a person of skill in the art. Both the number of hours of freezing and/or thawing can be varied as well as the number of cycles (see Table 1).

The ideal parameters for this method are found in Table 1 in the column for meniscus.

It will be appreciated that other types of devices other than loading frame 700 can be used to apply the targeted forces to the polymer in the manner described herein.

Mold and Loading Frame for a Method for Making, Manufacturing and/or Producing Engineered Meniscus A further aspect of the current invention is the unique mold and loading frame used in the method of making, manufacturing and/or producing engineered meniscus.

In one embodiment shown in FIG. 6, the mold 500 is composed of an inlet port 510, an outlet port 520, a well 530 for holding the polymer 100, and an area 540 for a rigid porous base 600.

After the polymer is removed from the mold 500, the polymer 100 and rigid porous base 600 are loaded on a loading frame 700. In one embodiment shown in FIG. 7, the loading frame 700 is composed of a base 760, the post 740, the crank 730, at least one worm 750, at least one worm gear 770, at least one set screw 720 and at least one lead screw 710. The worm 750 and worm gear 760 are mechanical means for causing the controlled movement of the screws 720 based on rotation of the crank 730 so as to impart motion to the rigid porous bases 600 since the bases 600 are fixed (anchored) to the set screws 720 (which in turn are coupled to the set screws 710).

The mold can be made using traditional manufacturing from Teflon, PEEK, PEKK, polycarbonate or ULTEM with polycarbonate being the preferred material. The mold can also be manufactured using newer technologies such as 3D printing.

Additionally, the mold and loading frame can be made of material able to withstand freezing temperatures, change in temperatures, chemical crosslinking agents, and exposure to UV light.

The mold can be created to house a triangular cavity with width of about 5 mm to about 20 mm, height of about 3 to about 8 mm, and length of about 70 mm to about 100 mm. The loading frame can include a post with a radius of about 5 mm to about 15 mm and the ability to apply from about 10% to about 50% strain to the polymer.

Engineered Orthopedic Soft Tissue

The current invention also provides for the engineered orthopedic soft tissue which is made, manufactured and/or produced by the methods and systems disclosed herein.

In one embodiment, the engineered orthopedic soft tissue is cartilage and has the fiber alignment of naturally occurring cartilage including a superficial tangential zone, a middle zone, and a deep zone. See FIG. 5.

In a further embodiment, the engineered orthopedic soft tissue is meniscus and has the fiber alignment of naturally occurring cartilage. See FIG. 8. In some embodiments, the engineered meniscus is attached to at least one rigid porous base.

In a further embodiment, the engineered orthopedic soft tissue is annulus fibrosus and had the fiber alignment of naturally occurring cartilage. In some embodiment, the engineered annulus fibrosus is attached to a hydrogel which mimics or is a replacement for nucleus pulposus.

In yet a further embodiment, the engineered orthopedic soft tissue is tendon and ligament and has the fiber alignment of naturally occurring tendon and ligament.

In some embodiments, the engineered orthopedic soft tissue is used alone to treat, repair and/or replace defects and/or injuries to biological tissue, more specifically to musculoskeletal tissue, more specifically orthopedic soft tissue.

In some embodiments, the engineered orthopedic soft tissue is used in combination with or attached to at least one rigid porous base to treat, repair and/or replace defects and/or injuries to biological tissue, more specifically to musculoskeletal tissue including both orthopedic soft tissue and rigid material such as bone.

In some embodiments, the engineered orthopedic soft tissue is used in combination with or attached to another polymer or native tissue by mechanical attachment (i.e. sutures, screws, or a rigid material), chemical attachment (i.e. formaldehyde, glutaraldehyde), or UV attachment (i.e. methacrylation of the polymer and redox reagents).

In further embodiments, the engineered orthopedic soft tissue is used in combination with an additional polymer, hydrogel or cryogel to treat, repair and/or replace defects and/or injuries to biological tissue, more specifically to musculoskeletal tissue.

Kits

The current invention also provides for kits which includes the materials needed to practice the novel method of making, manufacturing and/or producing engineered cartilage.

In one embodiment, the kit comprises a mold 200 and the leaflet expander 400 of the invention for making, manufacturing and/or producing engineered cartilage.

In another embodiment, the kit comprises a mold 500 and loading frame 700 of the invention for making, manufacturing and/or producing engineered meniscus.

In further embodiments, the kit provides starting materials for the methods including polymers and when necessary rigid porous bases.

In some embodiments, instructions are included in the kit. Such instruction can include information regarding the assembly of the mold, and expander or loading frame, with the various components, and parameters for crosslinking the polymer either by freezing and thawing including time, temperature and number of cycles, chemical concentration and exposure time, or exposure to UV light.

EXAMPLES

The present invention may be better understood by reference to the following non-limiting examples, which are presented in order to more fully illustrate the preferred embodiments of the invention. They should in no way be construed to limit the broad scope of the invention.

Example 1—Assembly of Mold for Making Engineered Cartilage Using Radial Forces The mold used in this method comprises four leaflets. The first step of the method is assembling the four leaflets radially into one hemispherical shaped mold.

Figure 5C:
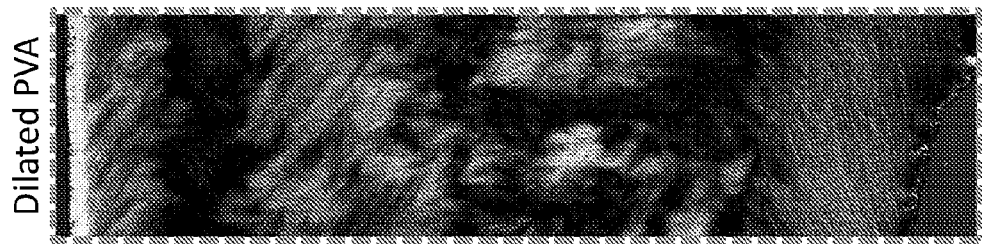
FIG. 5C is a polarized light image of the expanded polymer showing high birefringence on the top and bottom layers.
Figure 5B:
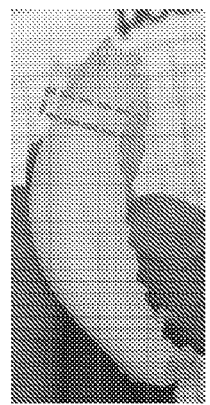
FIG. 5B is a cross-section of expanded polymer with red box denoting the location imaged under polarized light.

As shown in FIGS. 2 and 4, the four leaflet units contain a leaflet 210, a leaflet compression spring rod 240, and a tension spring 260 that are assembled radially and held together by a leaflet collar 220 to form a mold that is a hemisphere (FIG. 2). To assemble the mold, each leaflet 210 was attached to the central post 230 through a rod on the leaflet 240 that attached to a tube 250 in the central post 230 (FIG. 5B). The leaflets were then held together with a leaflet collar 220 (FIGS. 2A and 4B).

Example 2—Making Engineered Cartilage Using Radial Forces

Once the mold was assembled, it was placed into a hemispherical container 300 (FIG. 2B). Five (5) ml of 10% liquid poly(vinyl alcohol) was poured into the container 300 such that it surrounded the mold and formed a layer of uniform thickness on the surface of the mold 200.

The liquid polymer then underwent one freeze/thaw cycles which entailed the following steps: 1) ramping down to −20° C. at a rate of 0.5° C./min; 2) when a temperature of −20° C. was reached, the chamber was held at −20° C. for 20 hours after which; 3) the temperature was ramped to 20° C. at a rate of 0.5° C./min and held for 4 hours. This creates a partially crosslinked polymer network with randomly aligned polymer chains.

The partially crosslinked polymer 100 and mold 200 were removed from the container 300 and the leaflet collar 220 removed. The central post 230 of the mold 200 was then screwed onto the hemispherical leaflet expander 400. The leaflet expander contained a central threaded component 410 that acted to advance the hemisphere up the central post (FIG. 3) and radially expanded the polymer 100 cast on the mold 200. The expansion rate was controlled to create a strain rate of 1%/sec until a strain of 40% was reached. The expanded mold then underwent five remaining freeze/thaw cycles as described.

Example 3—Removal of PVA from the Mold and Testing of Fiber Alignment

After expanding the PVA, the randomly aligned polymer chains crosslinked in the partially crosslinked PVA aligned with directions of strain and were fixed in their strained positions by further crosslinking which created new randomly crosslinked chains.

Figure 5A:
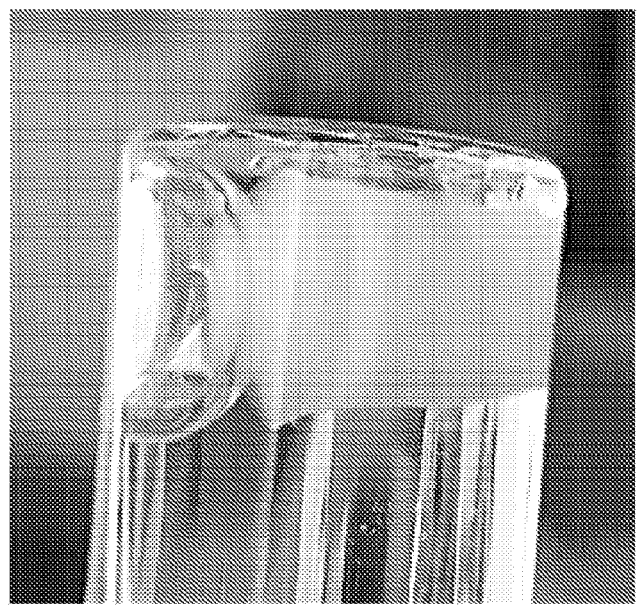
FIG. 5A is an 8 mm biopsy punch of the polymer after expansion showing three distinct layers.

After completion of the remaining crosslinking processes, the PVA was removed from the mold and kept hydrated in water. After expansion, the engineered cartilage shows three distinct layers similar to naturally occurring cartilage (FIG. 5A).

Cross-sections of the PVA (FIG. 5B) were imaged under polarized light. 100 μm sections of the PVA were taken by first cutting the expanded and crosslinked PVA into eighths along its radius and then freezing one of the eight pieces containing the cut edges on a freezing stage attached to a sledge microtome. After the PVA slice was completely frozen, a 100 μm section was taken and placed on a microscope slide. The slide was then imaged under circular polarized light to visualize the alignment of the polymer chains.

Figure 5D:
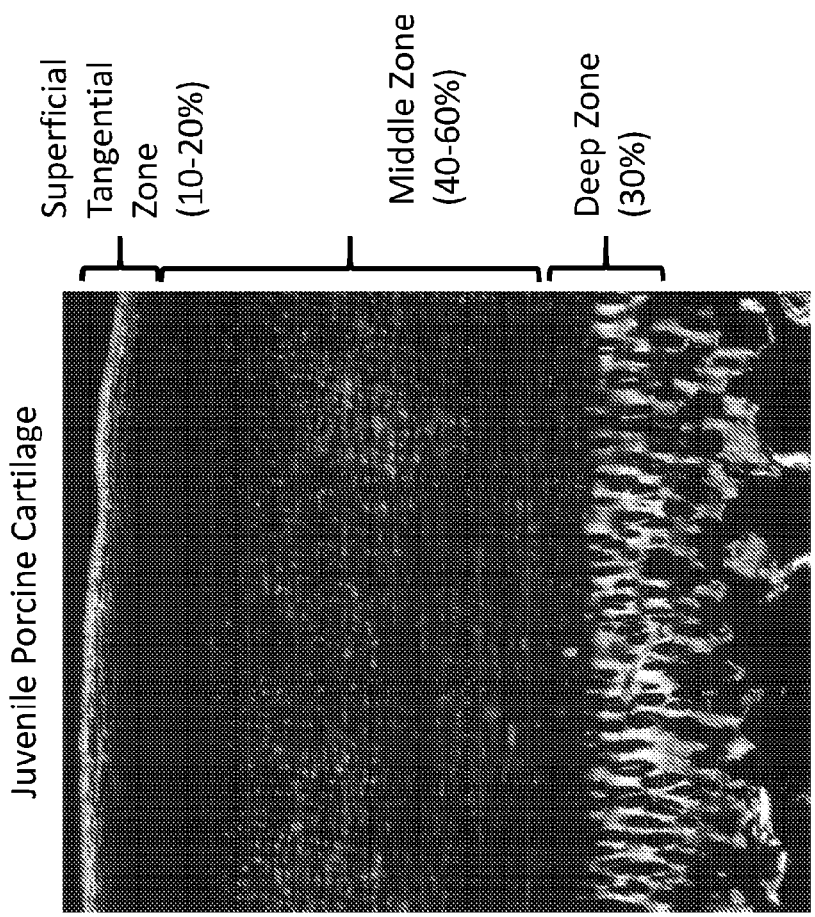
FIG. 5D is a representative image of the birefringence pattern of cartilage from newborn porcine articular cartilage.

As shown in FIG. 5, the engineered cartilage made in Example 2 (FIG. 5C) has distinct regions under polarized light which resembled the alignment of naturally occurring articular cartilage (FIG. 5D).

Example 4—Making Engineered Meniscus

A negative mold 500 shown in FIGS. 6A and 6B was used to cast the polymer into the desired shape. The mold consists of an inlet port 510, outlet port 520, and areas to place rigid porous bases for integration with the polymer 540 and the polymer 530.

Liquid PVA (20%) was injected with a syringe into the inlet port 510 until liquid polymer began to flow from the outlet port 520. The mold with liquid polymer was then placed into an environmental chamber and underwent one freeze/thaw cycles which entailed the following steps: 1) ramping down to −20° C. at a rate of 0.5° C./min; 2) when a temperature of −20° C. was reached, the chamber was held at −20° C. for 20 hours after which; 3) the temperature was ramped to 20° C. at a rate of 0.5° C./min and held for 4 hours. After 1 freeze/thaw cycle, the partially crosslinked polymer was removed from the mold. FIGS. 6C and 6D show the shape of the polymer and its cross section once removed from the mold.

Figure 7C:
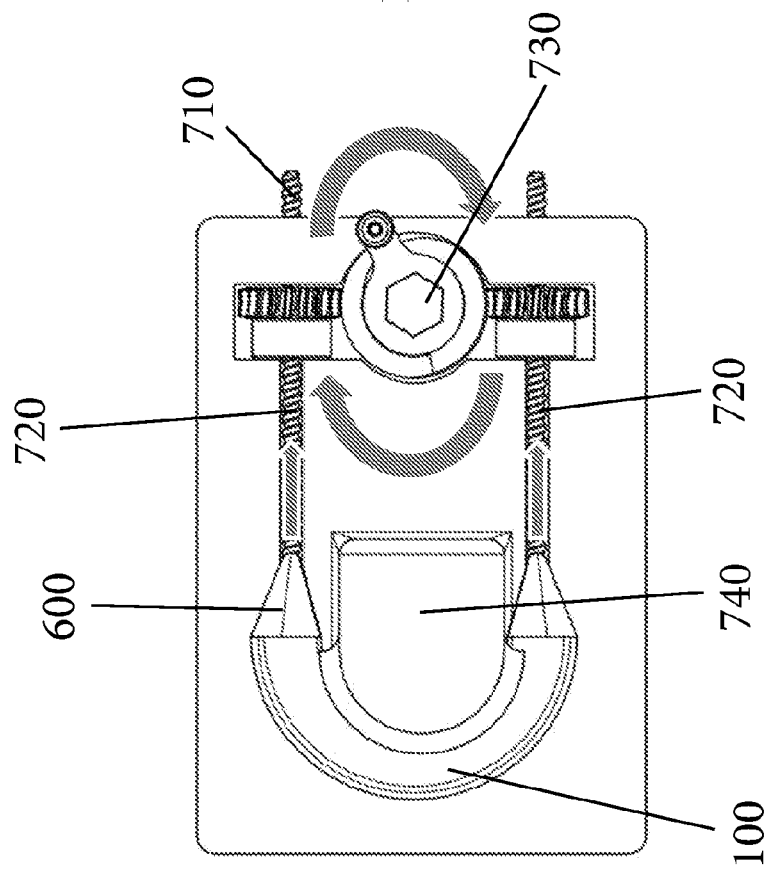
FIG. 7C is a top view of the loading frame showing the turning of the crank.

The partially crosslinked PVA polymer was then placed into the loading frame 700 and the rigid porous bases were fixed to the lead screws 710 on either side of the loading frame by set screws 720 (FIG. 7A). The crank was turned clockwise to cause the rigid porous bases 600 to move toward the crank (FIG. 7C). This caused a tensile force at the ends of the partially crosslinked polymer 100 and forced the polymer 100 against the post 740 that creates radial ($F_y$), axial ($F_z$), circumferential ($F_c$), compressive and tensile forces (FIG. 7D) that acts on the polymer. After stretching to 30% strain the PVA on the loading frame was placed by in the environmental chamber and underwent 5 more freeze/thaw cycles as described above.

Once the freeze/thaw cycles were complete, the fully crosslinked PVA cryogel was removed from the loading frame.

Polarized images of a 100 um thick slice of the cryogel shows circumferential alignment of the PVA cryogel (FIG. 8).

The invention claimed is:

1. A method of making, manufacturing and/or producing engineered orthopedic soft tissue comprising:
   forming a polymer into a predefined shape using a mold;
   partially crosslinking the polymer without aligning fibers of the polymer;
   applying at least one external force to the partially crosslinked polymer; and
   further crosslinking the partially crosslinked polymer while the at least one external force is applied under conditions and for a time to allow the fiber orientation of the engineered orthopedic soft tissue to mimic or recapitulate the fiber orientation of naturally occurring orthopedic soft tissue, and wherein application of the at least one external force to the partially crosslinked polymer induces two or more internal forces that act in different directions directly on the partially crosslinked polymer.

2. The method of claim 1, wherein the engineered orthopedic soft tissue is cartilage and the at least one external force comprises a radial force (FR) that is applied to the partially crosslinked polymer in multiple and different directions resulting in the two or more internal forces being a compressive force and a tensile force within the partially crosslinked polymer.

3. The method of claim 2, wherein the compressive force is located along an inner surface of the partially crosslinked polymer and the tensile force is located along an outer surface of the partially crosslinked polymer.

4. The method of claim 2, further including the step of positioning at least a portion of the partially crosslinked polymer against at least one surface and the step of applying the at least one external force to the partially crosslinked polymer comprises applying the at least one external force to the at least one surface, wherein the at least one surface comprises the mold which has a hemispherical shape.

5. The method of claim 4, wherein the step of applying at least one external force to the partially crosslinked polymer comprises coupling the mold onto an expander and radially expanding the mold due to contact between the expander and the mold.

6. The method of claim 1, wherein the engineered orthopedic soft tissue is meniscus and the at least one external force comprises a tensile force applied to the partially crosslinked polymer resulting in a combination of at least three internal forces acting directly on the partially crosslinked polymer in multiple and different directions, the at least three internal forces comprising a circumferential force (FC), a compressive force, and a tensile force.

7. The method of claim 6, wherein the partially crosslinked polymer comprises an elongated structure with rigid porous bases at opposite ends thereof and the step of applying at least one external force to partially crosslinked polymer comprises: placing the partially crosslinked polymer with the rigid porous bases in a loading frame; and pulling on the rigid porous bases to cause the elongated structure to seat against a post that comprises the at least one surface resulting in creation of the circumferential force (FC), the compressive force, and the tensile force within the partially crosslinked polymer.

8. The method of claim 7, wherein the step of pulling on the rigid porous bases comprises the steps of fixing the rigid porous bases to screws and rotating a crank of the loading frame to cause movement of the screws and pulling of the rigid porous bases.

9. The method of claim 1, wherein the engineered orthopedic soft tissue is annulus fibrosus and the at least one external force comprises a torsional force and a compressive force applied in multiple and different directions to the partially crosslinked polymer resulting in internal forces that comprise tensile forces that act in multiple directions on the partially crosslinked polymer.

10. The method of claim 1, wherein the engineered orthopedic soft tissue is tendons and ligaments and the at least one external force comprises torsional forces ($F\tau$) and tensile forces applied in multiple and different directions to the partially crosslinked polymer and the two or more internal forces comprise tensile forces.

11. The method of claim 1, further including the step of positioning at least a portion of the partially crosslinked polymer against at least one surface and the step of applying the at least one external force to the partially crosslinked polymer comprises applying the at least one external force to the at least one surface.

12. The method of claim 1, wherein the polymer is chosen from the group consisting of poly (vinyl alcohol) (PVA), polyurethane, polycarbonate urethane, ultrahigh molecular weight polyethylene, polyacrylic acid, collagen, chitosan, hyaluronic acid and any other synthetic or natural polymer.

13. The method of claim 1, wherein the polymer concentration ranges from about 10% to about 40%.

14. The method of claim 1, wherein the crosslinking is done by one or more freeze/thaw cycles, exposure to a chemical agent, or exposure to UV light.

15. The method of claim 1, wherein the freeze/thaw cycle comprises the steps of:
   ramping the temperature to about −20° C. at a rate of about 0.5° C./minute;
   freezing the polymer at about −20° C. for about 4 to about 24 hours;
   ramping the temperature to about 20° C. at a rate of about 0.5° C./minute; and
   thawing the polymer at about 20° C. for about 4 to about 12 hours.

16. The method of claim 1, wherein the polymer is attached or connected to an additional polymer, cryogel, or hydrogel, a rigid porous base, native tissue, or combinations thereof.

17. A method of making, manufacturing and/or producing engineered orthopedic soft tissue comprising:
   applying more than one force to a polymer and crosslinking the polymer while the more than one forces are applied under conditions and for a time to allow fiber orientation of the engineered orthopedic soft tissue to mimic or recapitulate the fiber orientation of naturally occurring orthopedic soft tissue and wherein the more than one forces are applied in multiple and different directions,
   wherein the crosslinking is done by one or more freeze/thaw cycles, exposure to a chemical agent, or exposure to UV light, and
   wherein the freeze/thaw cycle comprises the steps of:
   a. ramping the temperature to about −20° C. at a rate of about 0.5° C./minute;

b. freezing the polymer at about −20° C. for about 4 to about 24 hours;
c. ramping the temperature to about 20° C. at a rate of about 0.5° C./minute; and
d. thawing the polymer at about 20° C. for about 4 to about 12 hours.

* * * * *